(12) United States Patent
Baroud et al.

(10) Patent No.: US 9,095,392 B2
(45) Date of Patent: Aug. 4, 2015

(54) BONE CEMENT DELIVERY SYSTEM

(76) Inventors: Gamal Baroud, Canton-de-Hatley (CA); Denis Imbeault, Sherbrooke (CA); Mohamed Habib, Sherbrooke (CA)

( * ) Notice: Subject to any disclaimer, the term of this patent is extended or adjusted under 35 U.S.C. 154(b) by 205 days.

(21) Appl. No.: 13/463,349

(22) Filed: May 3, 2012

(65) Prior Publication Data
US 2013/0123790 A1    May 16, 2013

Related U.S. Application Data

(63) Continuation of application No. PCT/CA2010/001790, filed on Nov. 5, 2010.

(60) Provisional application No. 61/258,797, filed on Nov. 6, 2009.

(51) Int. Cl.
    *A61B 17/88*    (2006.01)

(52) U.S. Cl.
    CPC ......... *A61B 17/8822* (2013.01); *A61B 17/8819* (2013.01); *A61B 17/8833* (2013.01); *A61B 2017/883* (2013.01)

(58) Field of Classification Search
    CPC .................................................. A61B 17/8822
    USPC .......................................................... 606/94
    See application file for complete search history.

(56) References Cited

U.S. PATENT DOCUMENTS

| | | |
|---|---|---|
| 1,988,480 A | 1/1935 | Campkin |
| 2,602,446 A | 7/1952 | Glass et al. |
| 2,627,270 A | 2/1953 | Glass |
| 2,690,178 A | 9/1954 | Bickford |
| 2,702,547 A | 2/1955 | Glass |
| 3,623,474 A | 11/1971 | Hellman et al. |
| 3,631,847 A | 1/1972 | Hobbs et al. |
| 3,701,345 A | 10/1972 | Hellman et al. |
| 4,423,371 A | 12/1983 | Senturia et al. |
| 4,952,205 A | 8/1990 | Mauerer et al. |
| 5,007,904 A | 4/1991 | Densmore et al. |
| 5,681,286 A | 10/1997 | Niehoff |
| 5,947,929 A | 9/1999 | Trull |
| 6,241,734 B1 | 6/2001 | Scribner et al. |
| 6,368,307 B1 | 4/2002 | Ziemba et al. |
| 6,958,053 B1 | 10/2005 | Reilly |
| 7,008,433 B2 | 3/2006 | Voellmicke et al. |
| 7,465,290 B2 | 12/2008 | Reilly |
| 7,549,977 B2 | 6/2009 | Schriver et al. |
| 7,563,249 B2 | 7/2009 | Schriver et al. |
| 7,572,263 B2 | 8/2009 | Preissman |
| 7,662,133 B2 | 2/2010 | Scarborough et al. |

(Continued)

*Primary Examiner* — David Bates
(74) *Attorney, Agent, or Firm* — Norton Rose Fulbright Canada LLP

(57) ABSTRACT

A bone cement delivery unit having a rigid support structure with a first portion configured to engage and retain a bone cement reservoir against its casing, a second portion supporting a transmission system and a third portion supporting and guiding a slidable push rod along the injection direction. The delivery system may include a control unit sliding the push rod opposite to the injection direction before stopping the push rod if the quantity of the bone cement pushed out of the reservoir has reached at least a predetermined minimum value, such as to eliminate residual flow. Also, the delivery system may include an adaptor including members electrically connected to the control unit, with the cement reservoir including a sensor for monitoring curing of the bone cement in electrical contact with the members of the adaptor.

15 Claims, 10 Drawing Sheets

(56) References Cited

U.S. PATENT DOCUMENTS

| | | |
|---|---|---|
| 2005/0070915 A1 | 3/2005 | Mazzuca et al. |
| 2005/0113843 A1 | 5/2005 | Arramon |
| 2005/0177111 A1 | 8/2005 | Ozeri et al. |
| 2006/0074433 A1 | 4/2006 | McGill et al. |
| 2006/0079905 A1 | 4/2006 | Beyar et al. |
| 2007/0027230 A1 | 2/2007 | Beyar et al. |
| 2007/0149926 A1* | 6/2007 | Moberg et al. ................ 604/152 |
| 2007/0191858 A1 | 8/2007 | Truckai et al. |
| 2007/0233147 A1* | 10/2007 | Vendrely et al. ................ 606/92 |
| 2008/0195114 A1 | 8/2008 | Murphy |
| 2008/0249530 A1 | 10/2008 | Truckai et al. |

* cited by examiner

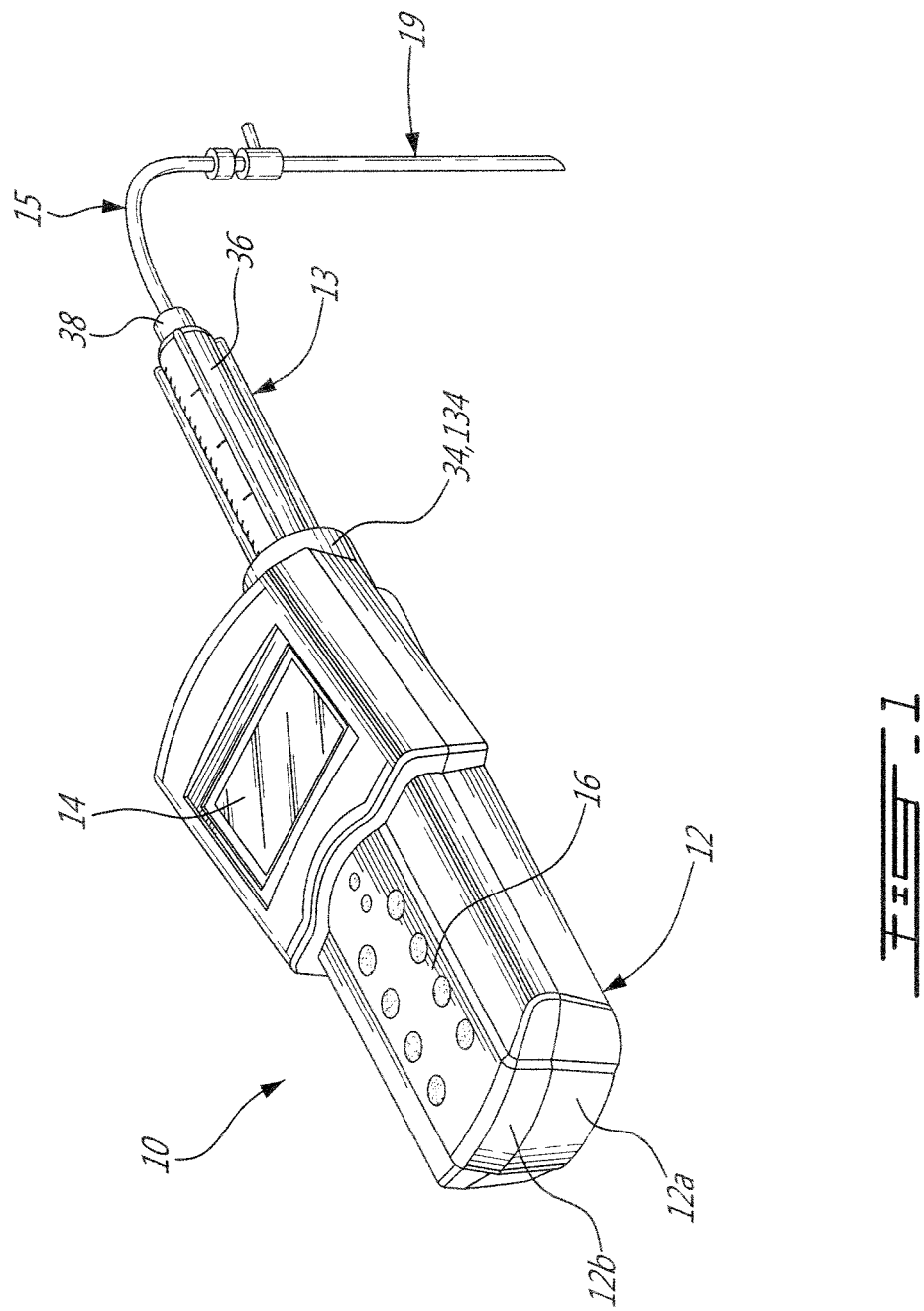

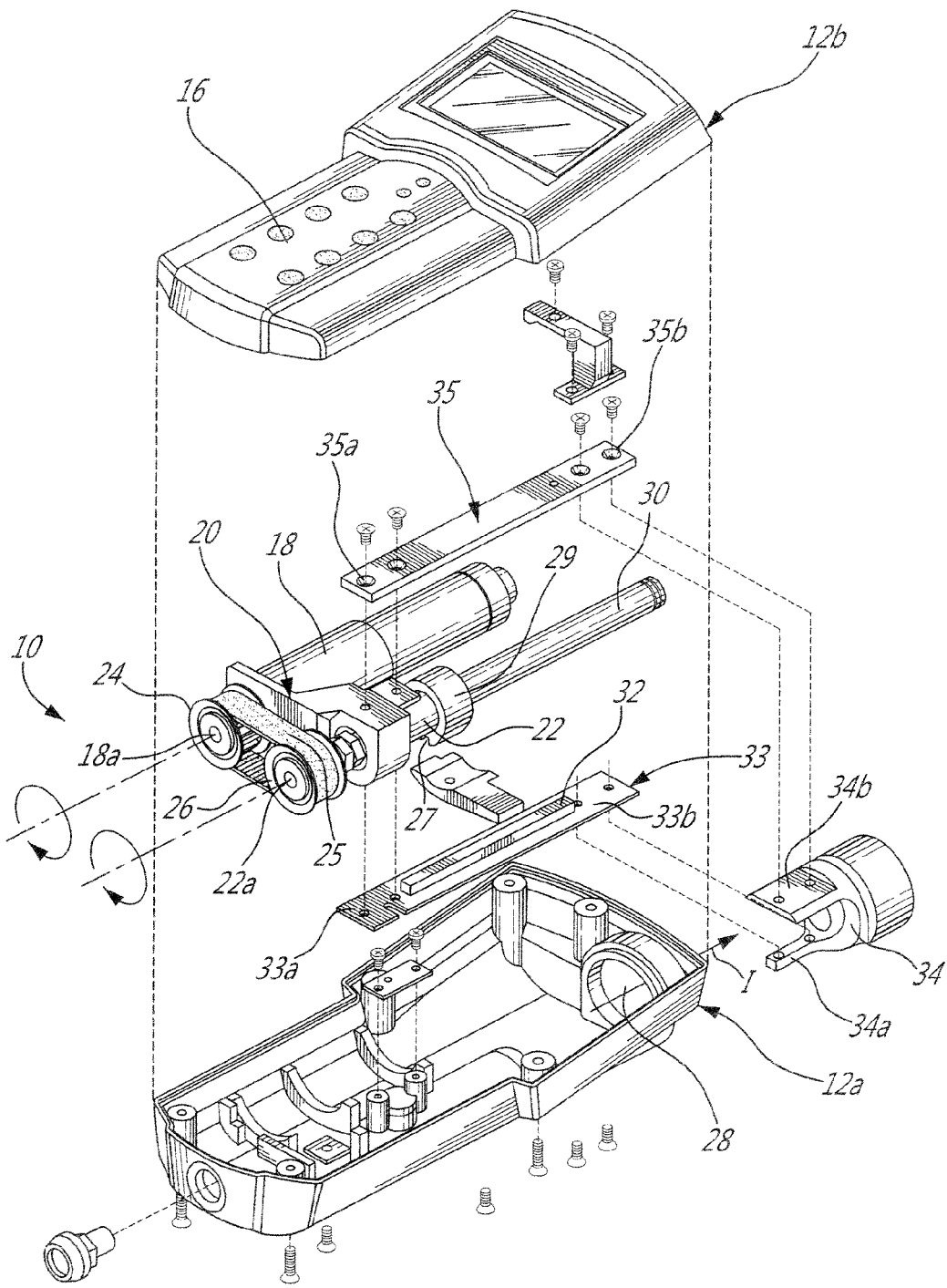

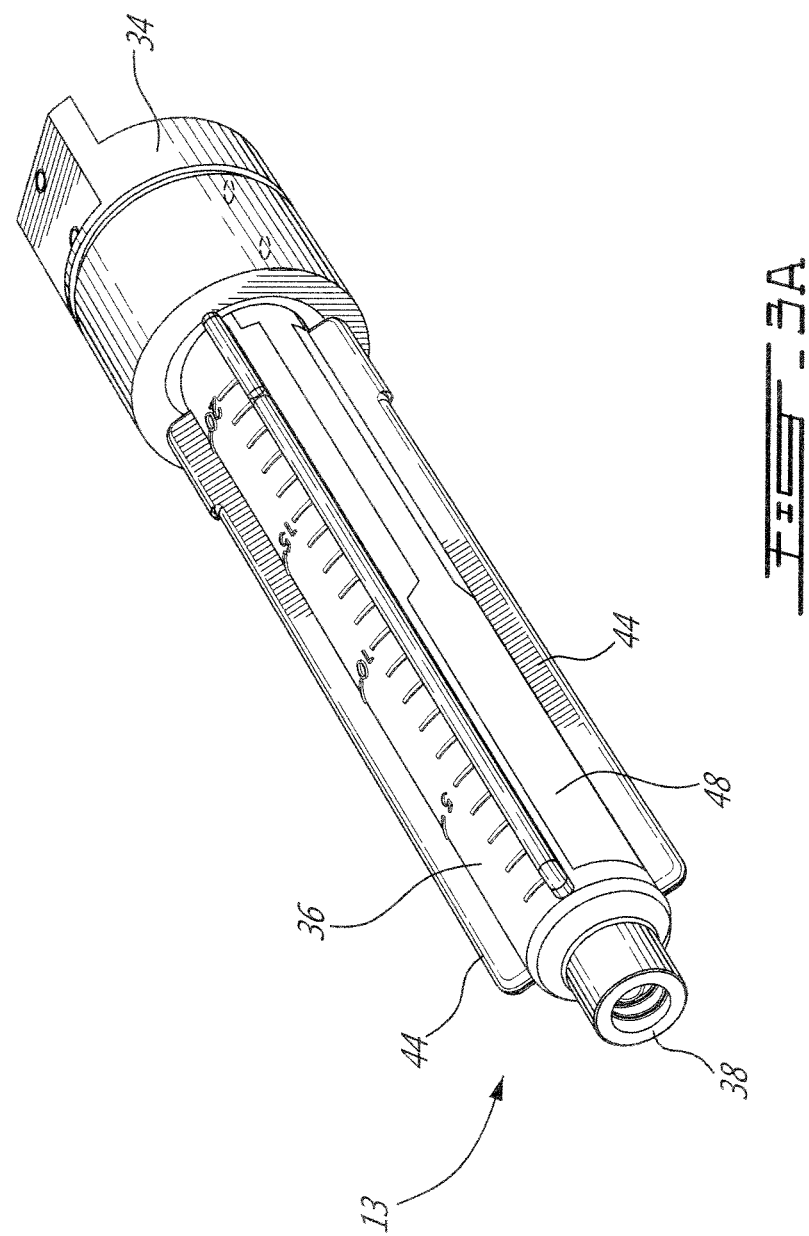

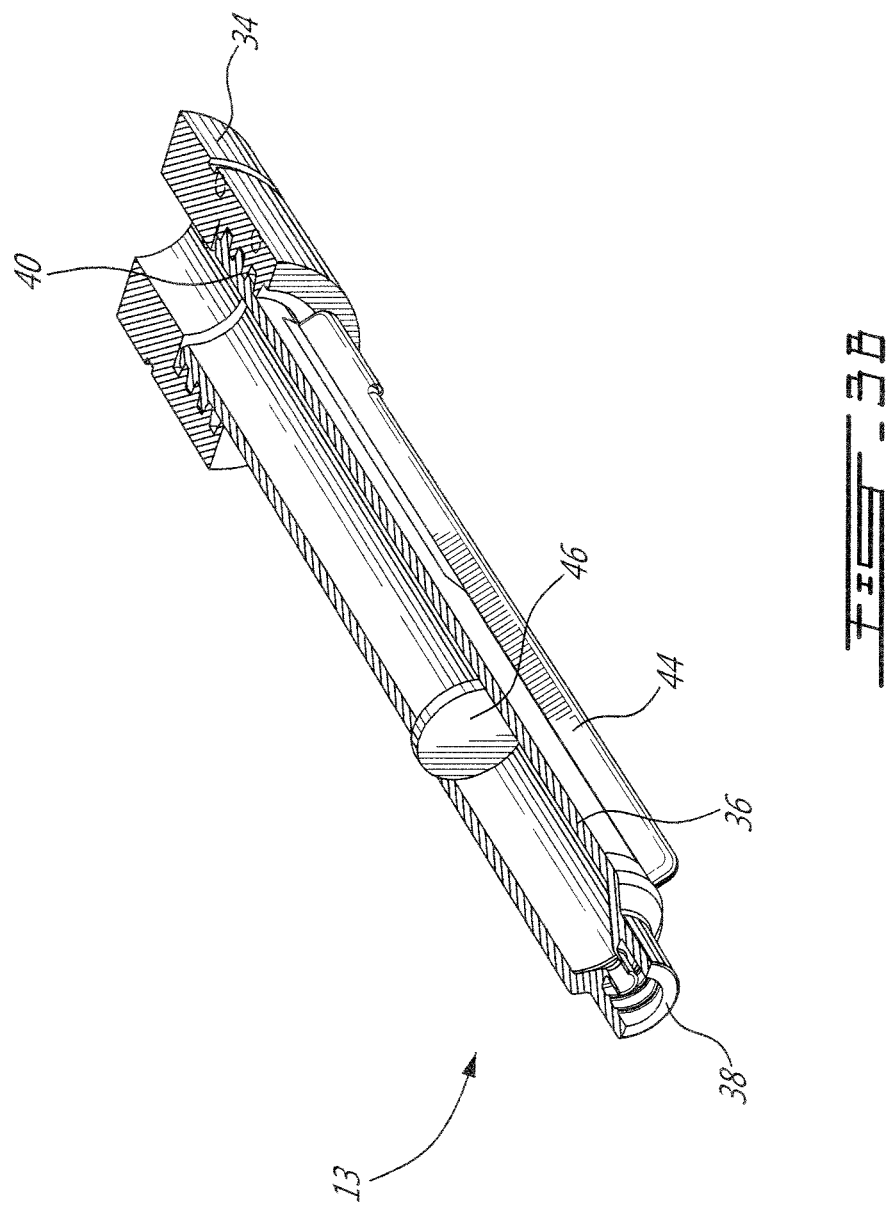

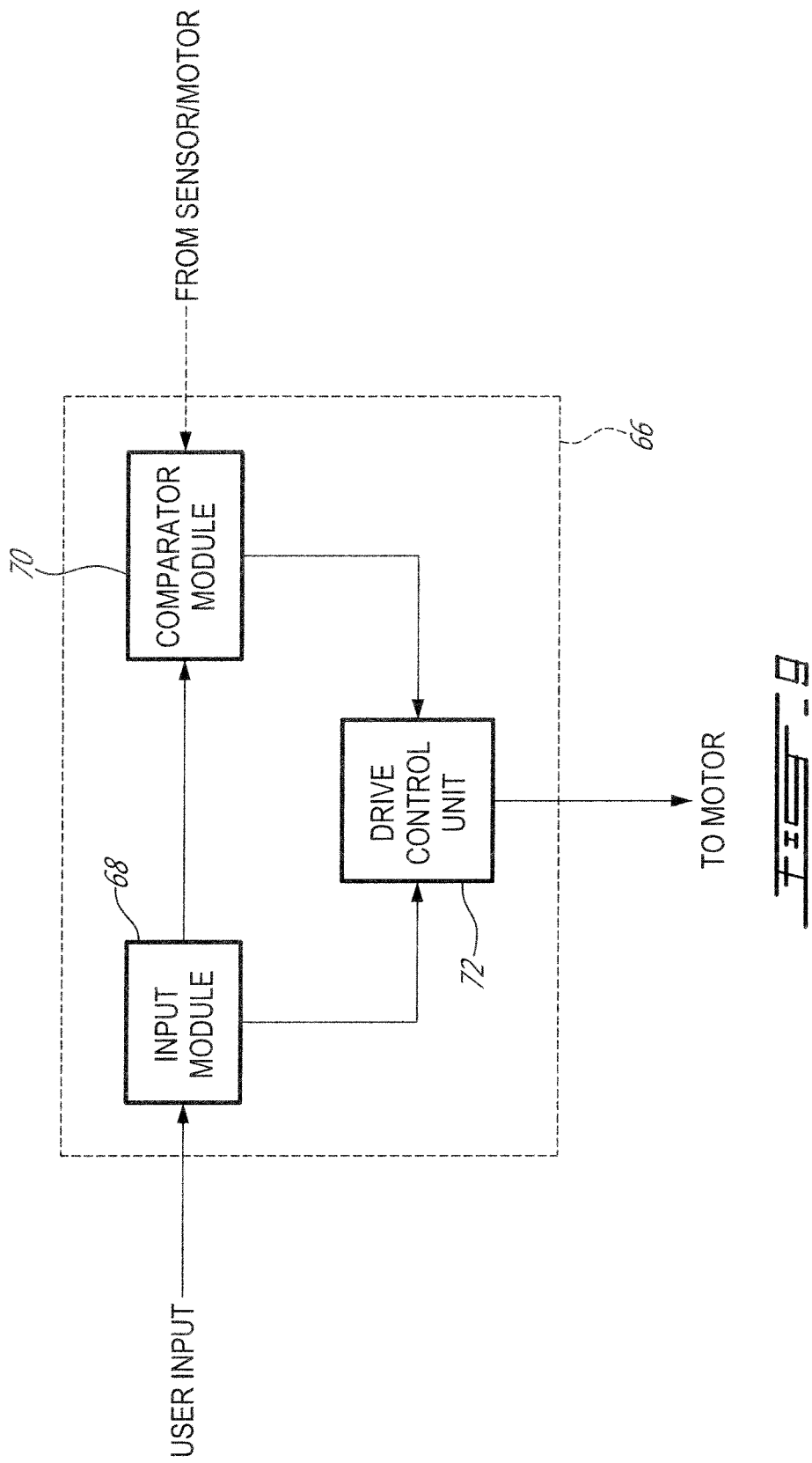

BONE CEMENT DELIVERY SYSTEM

CROSS-REFERENCE TO RELATED APPLICATIONS

The present application is a continuation of PCT Application No. PCT/CA2010/001790 filed on Nov. 5, 2010 which claims priority on U.S. Provisional Patent Application No. 61/258,797 filed on Nov. 6, 2009, the entire content of which is incorporated by reference herein.

FIELD OF THE INVENTION

The present invention relates to an apparatus and method for performing bone augmentation procedures, and more particularly to a cement delivery system for such procedures and to a method for the use of such a system.

BACKGROUND ART

Vertebroplasty has been developed to treat vertebral compression fractures, and consists of injecting medical bone cement under pressure through a cannula into a vertebral body. The bone is usually porous with bone marrow occupying the porous space. The cement injected into the vertebral body displaces the bone marrow and fills the bone cavity. The cement hardens in-situ providing mechanical strength and stability of the bone weakened by osteoporosis or other pathologies such as cancers.

Bone cements are usually formed by dispersing PMMA particles in a monomer. Once the particles and monomer are mixed together, the particles partially dissolve in the monomer and form an increasingly thick cohesive dough. This phase is often known as swelling. This phase is followed by a second phase: the polymerization of the cement, where the thick dough becomes a hard polymeric material. However, as the cement polymerizes, it becomes increasingly harder to inject. A number of procedures typically have to be aborted due to the high delivery pressure requirement, which results in insufficient or poor filling which may fail to augment the vertebral body adequately.

Another pertinent limitation related to cement leakage is the usual inability of physicians to stop the cement flow immediately when required. Due to the high injection pressure in the injection system and the viscous nature of the cement, important residual flow of the cement typically exists in the system even after the injection is stopped, and until the system is de-pressurized.

Accordingly, improvements are desirable.

SUMMARY

It is therefore an aim of the present invention to provide an improved cement delivery unit and cement delivery system.

It is also an aim of the present invention to provide an improved method of controlling cement flow from a bone cement delivery unit.

Therefore, in accordance with the present invention, there is provided a bone cement delivery unit comprising a casing having a guide opening defined therethrough, a push rod slidable within the casing and out of the opening along an injection direction, a motor, a transmission system transmitting power from the motor to the push rod for sliding the push rod along the injection direction, and a rigid support structure having a first portion configured to engage and retain a bone cement reservoir against the opening of the casing, a second portion supporting the transmission system and a third portion supporting and guiding the push rod along the injection direction.

Also in accordance with the present invention, there is provided a bone cement delivery system comprising a delivery unit having a casing containing a motor, a push rod driven by the motor to slide out of an opening of the casing, a control unit, an adaptor attached to the casing around the opening and including members electrically connected to the control unit, and a cement reservoir having a proximal end configured to engage the adaptor, the cement reservoir including a sensor for monitoring curing of the bone cement, the members of the adaptor being in electrical contact with the sensor when the proximal end is engaged to the adaptor.

Also in accordance with the present invention, there is provided a bone cement delivery system comprising a bone cement reservoir for containing the bone cement, a motor, a push rod driven by the motor and in sliding engagement with the reservoir to push the bone cement out of the reservoir, an input device for receiving commands from a user, and a control unit comprising a processor, a memory accessible by the processor, and at least one application coupled to the processor and configured for receiving the user commands from the input device, activating the motor to slide the push rod in an injection direction upon receipt of an injection command from the user, determining a quantity of bone cement pushed out of the reservoir, activating the motor to slide the push rod along a predetermined distance in a direction opposite to the injection direction and then stop the motor upon receipt of a stop command from the user if the quantity of the bone cement pushed out of the reservoir has reached at least a predetermined minimum value, and stopping the motor to directly stop the push rod upon receipt of the stop command from the user if the quantity of the bone cement pushed out of the reservoir is below the predetermined minimum value.

Further in accordance with the present invention, there is provided a method of controlling cement flow from a bone cement delivery unit, comprising receiving an injection command from a user indicating the beginning of the cement injection, upon receipt of the injection command, actuating a push rod of the injection unit to push bone cement out of a cement reservoir attached thereto, receiving a stop command from a user indicating the end of the cement injection, and upon receipt of the stop command, if a quantity of the bone cement pushed out of the reservoir has reached at least a predetermined minimum value, reversing a movement of the push rod along a predetermined distance and then stopping the movement of the push rod.

BRIEF DESCRIPTION OF THE DRAWINGS

Reference will now be made to the accompanying drawings, showing by way of illustration a particular embodiment of the present invention and in which:

FIG. 1 is a schematic oblique view of a bone cement delivery system in accordance with a particular embodiment;

FIG. 2 is an exploded view of the delivery unit of the system of FIG. 1 in accordance with a particular embodiment;

FIG. 3A is an oblique view of a syringe and adaptor used with the delivery unit of FIG. 1;

FIG. 3B is a cross sectional oblique view the syringe and adaptor of FIG. 3A;

FIG. 9 illustrates an exemplary embodiment of an application of the control unit of FIG. 8.

DETAILED DESCRIPTION OF PARTICULAR EMBODIMENTS

Figure 4:
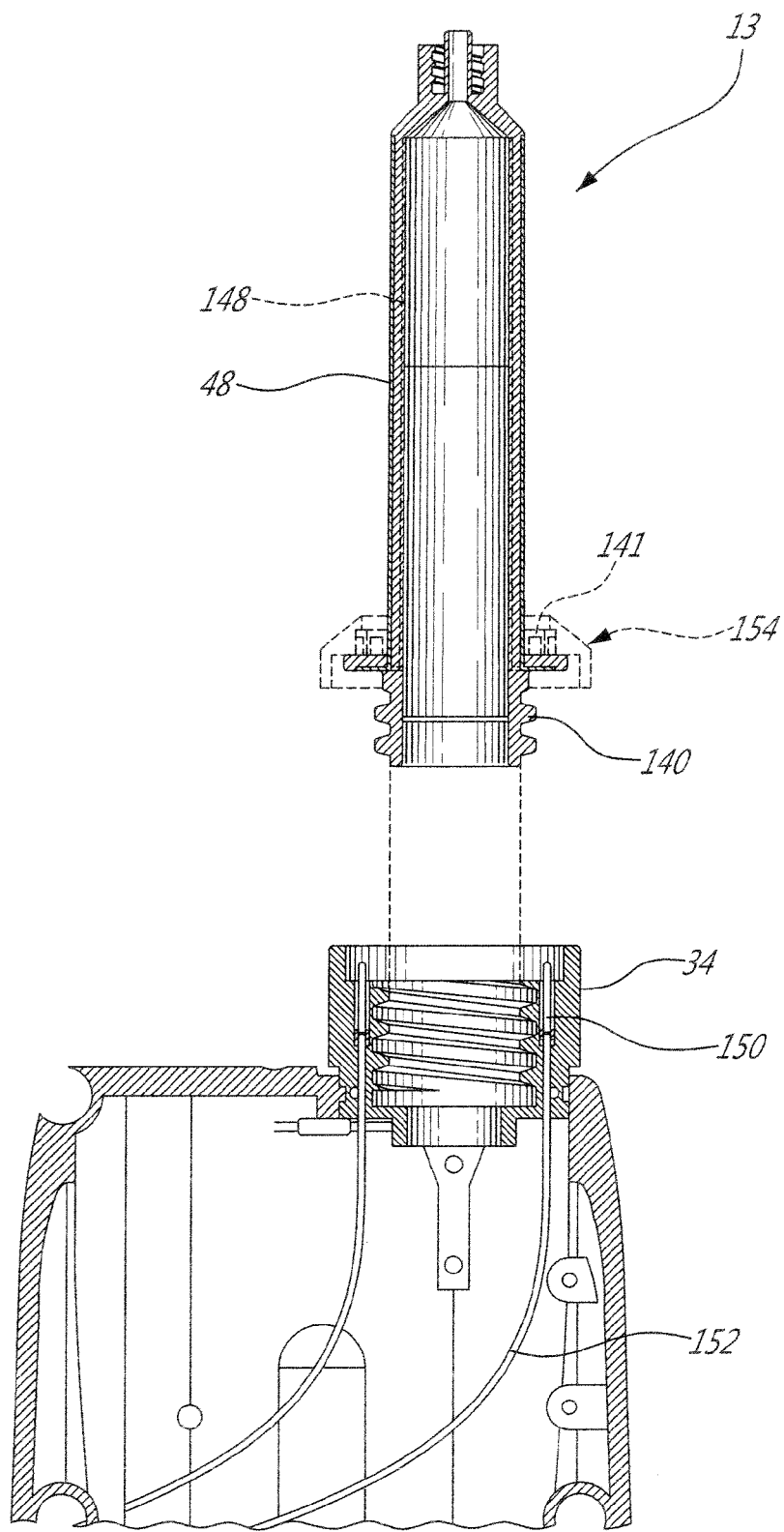
FIG. 4 is a cross-sectional view of a the syringe and adaptor of FIGS. 3A-3B, with part of the delivery unit shown.

The present invention is an improvement on the system disclosed in published PCT application WO 2007/115402 A1 filed Apr. 5, 2007, which is incorporated by reference herein.

FIG. 1 shows an embodiment of a bone cement delivery system, comprising a precision delivery unit 10 including a display screen 14 and an input device 16 which is shown here as a touch pad, a syringe or reservoir 13 fixedly connected to a casing 12 of the delivery unit 10, a cannula 19, and a high pressure flexible tube 15 connecting a distal end 38 of the reservoir 13 to the cannula 19.

In a particular embodiment, the flexible tube 15 is made of Nylon 12 and includes at each end a rotating luer lock adaptor which may be made of ABS. The cannula 19 is inserted into a vertebra, through a pedicle (not shown) in order to inject the bone cement, e.g. PMMA, into the vertebra.

In a particular embodiment, a remote control unit (not shown) is provided to activate the delivery unit 10 from a distance, including a touch pad or other input element allowing the same input as the touch pad 16 of the delivery unit 10, and a display screen allowing the display of the same data shown on the screen 14 of the delivery unit 10.

The casing 12 of the delivery unit includes separable bottom and top portions 12a and 12b. The casing portions 12a and 12b are preferably made of a sturdy medical grade plastic, to insure cleanness and freedom from bacteria. A gasket (not shown) is placed between the two casing portions 12a, 12b when assembled. A guide opening 28 (see FIG. 2) is defined in the casing 12 and a socket adaptor 34, 134 is provided around the opening 28 to removably receive the reservoir 13. An o-ring (not shown) provides a hermetic seal at the connection of the reservoir 13 and the socket adapter 34, 134.

As can be seen in FIG. 2, the delivery unit 10 includes a transverse support element 20 extending across the casing 12 along a transverse direction with respect to the injection direction I. The delivery unit 10 includes an electrically driven motor 18 fixedly mounted to the transverse support element 20. In a particular embodiment, the motor 18 is a 12V DC motor. A drive shaft 18a extending from the motor 18 and rotationally driven thereby passes through the transverse support element 20 and mounts a pulley 24.

A second pulley 26 is engaged to the first pulley 24 through a belt 25 (see FIG. 2) such as to rotate therewith. The second pulley 26 is mounted on a shaft 22a which is coaxial with a lead screw 22 and connected thereto such as to rotate integrally therewith. The lead screw 22 is supported by the transverse support element 20, for example through a bearing assembly, and extends on the same side of the support element 20 as the motor 18. The lead screw 22 and drive shaft 18a are preferably parallel.

The lead screw 22 is threadingly engaged inside an internally threaded push rod 30, such that the pulleys 24, 26, belt 25 and lead screw 22 define a transmission system transmitting power from the motor 18 to the push rod 30.

The end 29 of the push rod 30 closest to the transverse support element 20 is enlarged and includes an engagement slot 27 defined therein. The slot 27 engages a guiding track 32 defining the path of the movement of the push rod 30. The guiding track 32 prevents the push rod 30 from rotating with the lead screw 22, such that the push rod 30 is slidable in the injection direction I and back through the opening 28.

Alternate configurations are also possible for the transmission system, for example such as shown in PCT application WO 2007/115402. The transmission system may include, for example, a worm gear speed reduction mechanism powered by the motor and rotating a threaded rod, with a threaded component engaged to the threaded rod and retained such as to move linearly when the threaded rod is rotated. The threaded component is either part of the push rod or connected thereto, such that the linear motion of the threaded component moves the push rod in the injection direction and back. The transmission system may alternately include a spur gear and toothed rack speed reduction mechanism connected to the motor through a pinion. The toothed rack is either part of the push rod or connected thereto, such that the linear motion of the toothed rack moves the push rod in the injection direction and back. Other configurations are also possible.

The guiding track 32 is rigidly connected on top of, or integrally formed with, a lower support plate 33 which extends along the bottom of the casing 12, under the push rod 30. Referring to FIG. 2, the lower support plate 33 has a first end 33a rigidly connected to the transverse support element 20 and an opposed second end 33b rigidly connected to a lower connecting portion 34a of the socket adaptor 34. Similarly, an upper support plate 35 extends over the push rod 30 and has a first end 35a rigidly connected to the transverse support element 20 and an opposed second end 35b rigidly connected to an upper connecting portion 34b of the socket adaptor 34.

As such, the support plates 33, 35 and guiding track 32 interconnect the transverse support element 20 and the socket adaptor 34, defining a support structure directing the push rod 30 along its path and supporting the loads produced on the push rod 30 during cement injection. Alternate configurations for the support structure are also possible. For example, the support plates 33 and 35 can extend on each side of the push rod 30, or the support plates 33, 35, transverse support element 20 and socket adaptor 34 can be made of a single piece, with the guiding track 32 being manufactured separately or as part of the single piece. Other configurations are also possible. The portions of the support structure are rigidly interconnected (with a unitary construction being considered here a rigid connection as well) and are made of a material adapted to resist to the loads applied thereto. In a particular embodiment, the elements of the support structure, which in the embodiment shown correspond to the support plates 33, 35, the track 32, the transverse support element 20 and the socket adaptor 34, are made of an appropriate type of metal, for example stainless steel. Alternate adequate metals can also be used, including for example magnesium. The support structure is preferably attached to the casing 12 to prevent movement relative thereto, for example by small screws connecting the transverse support element 20 and lower support plate 33 to the bottom casing portion 12a.

Referring to FIGS. 3A-3B, the reservoir 13 includes a cylindrical body 36 having a distal port 38 to be connected to the cannula 19 through the flexible tube 15 (shown in FIG. 1). In a particular embodiment, the distal port 38 includes a luer-lock adaptor. The reservoir 13 is filled through the help of a syringe engaged to the distal port 38, before connection to the flexible tube 15. The cylindrical body 36 includes an open proximal end 40 threadingly engaged to the socket adaptor 34. Reinforcing ribs 44 extend along the length of the body 36 in order to provide additional rigidity to the reservoir 13, to withstand the pressure applied to the cement during injection.

In a particular embodiment, the cylindrical body 36 of the reservoir 13 is made of polycarbonate and has an 18 ml capacity, while the distal port 38 is defined by a stainless steel tip. Alternate adequate sizes and materials can also be used.

A piston 46 is added in the body 36 once it is filled with cement, and the piston 46 engages the push rod 30. When the lead screw 22 rotates, the push rod 30 advances linearly, i.e. slides on the guide track 32, pushing the piston 46 and thus forcing the cement into the cannula 19. In the preferred embodiment, the push rod 30 is connected to the piston 46 in a manner allowing the push rod 30 to pull the piston 46, for example through a threaded connection. The separate piston 46 and push rod 30 allow the push rod 30 to stay out of contact of the cement, and as such to be reusable after an injection. In an alternate embodiment, the piston 46 is an integral part of the push rod 30.

Still referring to FIG. 3A, the reservoir 13 includes two electro-conductive plates 48 which are located on the outer surface of the reservoir 13 and opposite one another; two electro-conductive plates 148 may alternately be provided on the inner surface of the reservoir 13 and opposite one another, as illustrated in phantom in FIG. 4. It is understood that only one of the illustrated set of plates 48, 148 is provided, the purpose of which will be described further below.

Referring to FIG. 4, the reservoir 13 includes an externally threaded proximal end 140 threadingly engaging the socket adaptor 34, which is formed separately of the casing 12. The socket adaptor 34 includes two spring-loaded protruding pins 150 connected to an electrical source through electrical wires 152. The reservoir 13 includes a hard stop limiting the travel thereof within the socket adaptor 34 to a position where the pins 150 are in contact with the plates 48 or 148 to provide an electrical connection.

The reservoir 13 optionally includes a second externally threaded portion 141 located distally of the threaded proximal end 140, and a base sleeve 154 is threadingly engaged to this second externally threaded portion 141 (not shown in FIGS. 3A-3B). The base sleeve 154 acts to isolate the part of the reservoir 13 that is contaminated upon fixation to the delivery unit 10, such as to preserve sterility. In a particular embodiment, a sterile drape (not shown) is placed on a base of the base sleeve 154 and pulled over the delivery unit 10 to prevent contamination of the sterile field.

Figure 5:
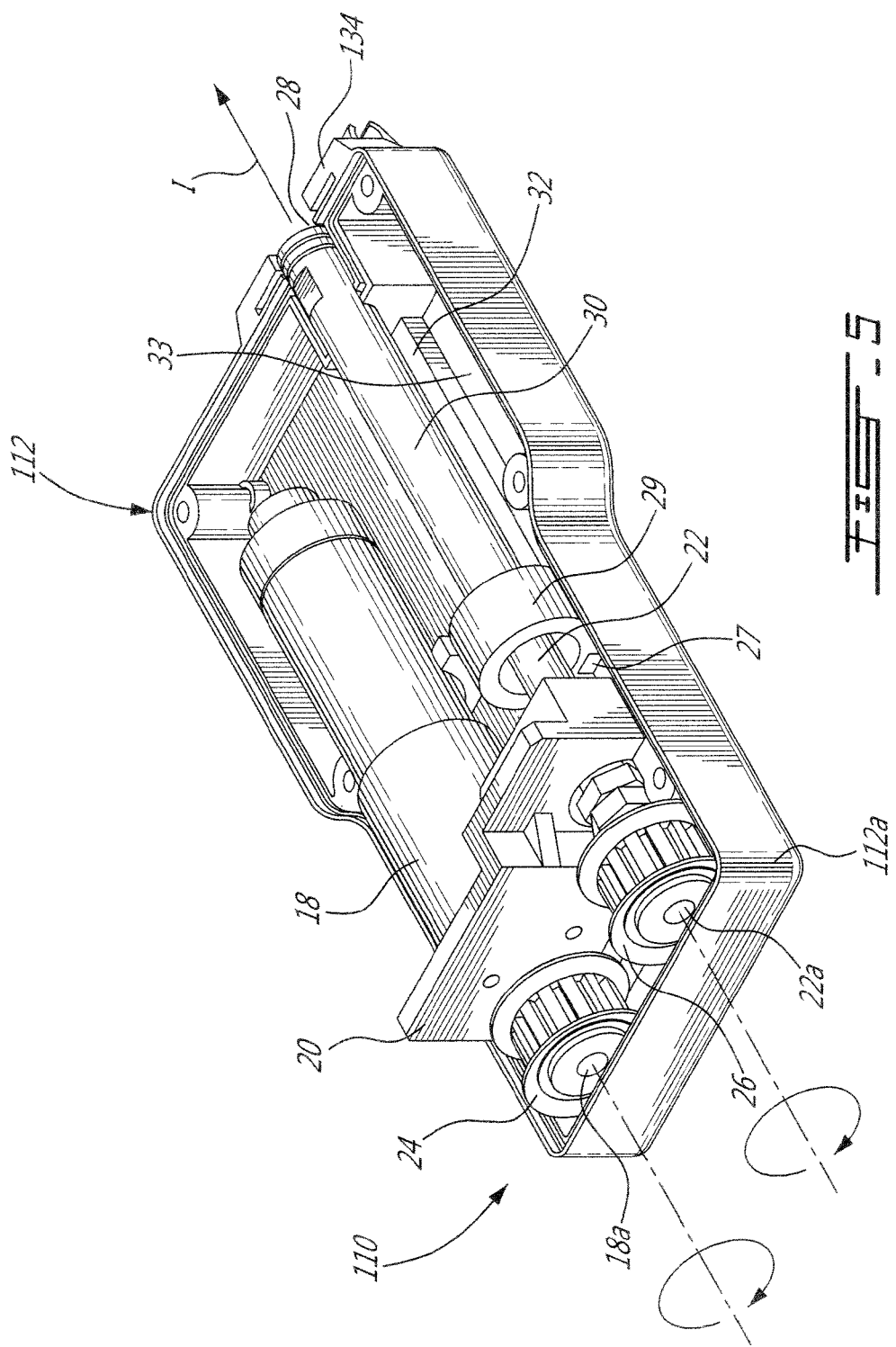
FIG. 5 is an oblique view of part of the delivery unit of the system of FIG. 1 in accordance with an alternate embodiment.

Referring to FIG. 5, an alternate embodiment for the delivery unit 110 is shown, with elements similar to the previous embodiment being identified by the same reference numerals; description of these elements will not be repeated herein. Also, the elements that are not depicted in FIG. 5 are similar to the corresponding elements of the previous embodiment. The main difference between FIG. 5 and the previous embodiment lies in the configuration of the socket adaptor 134: it is formed unitarily with the bottom portion 112a of the casing 112, and is configured to receive the cement reservoir through a bayonet type connection. The socket adaptor 134 is connected to the transverse support element 20 through the lower and upper support plates 33, 35, to define a support structure as previously described. The socket adaptor 134 may include spring loaded pins 150 as described above.

Figure 8:
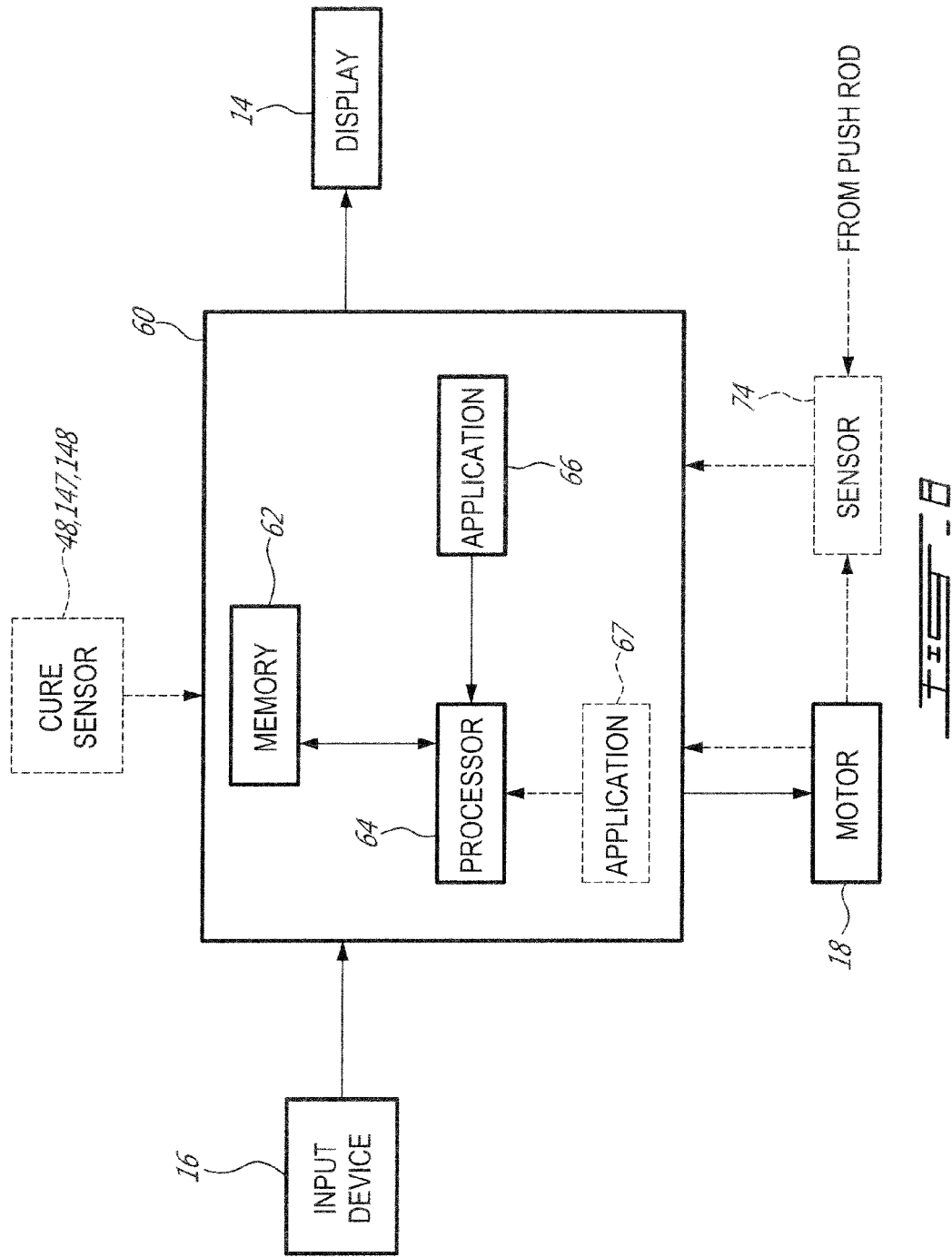
FIG. 8 is a block diagram of an exemplary embodiment of the bone cement delivery system of FIG. 1.

Referring to FIG. 8, the delivery unit 10 includes a control unit 60 which operates the motor 18 based on commands from the user on the input device 16 (for example shown in FIG. 1 as a touch pad of the delivery unit 10), and generates the output data displayed on the display unit 14 (for example shown in FIG. 1 as a screen on the delivery unit 10). The control unit 60 comprises an application 66 running on a processor 64, for example a microprocessor, the processor being coupled to a memory 62.

FIG. 9 shows an exemplary embodiment of the application 66 of the control unit 60. An input module receives an input signal from the input device 16, and interacts with a comparator module 70 and a drive control unit 72 by sending data thereto. The comparator module 70 receives data on the requested injection rate, and determines relevant cement flow rate and volume values. In one particular embodiment, the comparator module 70 receives data on the rotation of the motor output from the motor 18, and derives cement flow rate and volume values, such as current injection flow rate and amount of cement injected, from the rotation of the motor. In addition or alternately, the comparator module 70 may receive data from a sensor 74 measuring the push rod displacement and derives cement flow rate and volume values using this data. The comparator module 70 determines the motor rotation speed and direction corresponding to the requested injection rate, and sends a signal to the drive control unit which correspondingly activates or stops the rotation of the motor 18.

The control unit 60 thus controls the rotation of the motor 18 based on the commands of the user while ensuring that the push rod 30 moves at a constant speed, such that the cement injection is done at a constant selected rate. In a particular embodiment, the user can select an injection rate from 0.5 ml/min to 7 ml/min in increments of 0.5 ml/min. The delivery unit 10 thus provides injection of the cement in a controlled and continuous manner.

The cement flow rates and volume values may be displayed on the display unit 14, which in the embodiment shown corresponds to the screen of the delivery unit 10 but may also or alternately include the screen of the remote control unit if provided. Other data such as the time since the start of the injection may also be displayed.

In a particular embodiment, the control unit 60 includes a safety feature automatically slowing or stopping cement injection upon reaching a maximum predetermined pressure threshold, e.g. 3000 psi. This may be performed by the comparator module 70, receiving data from a pressure sensor 74 and sending a signal to the drive control unit to stop the motor 18 if the pressure exceeds the predetermined threshold. The pressure threshold is selected to be lower by a predetermined safety factor than the maximum pressure that can safely be applied by the delivery unit 10, taking into account the resistance of the components taking up the stresses caused by the pressurized cement, e.g. the support structure and reservoir.

If it is necessary to stop the cement delivery, the physician requires that the flow of cement be halted immediately when the signal is given to reduce the pressure. However, in typical injection systems, the high pressure within the system causes a residual flow of bone cement after the physician has stopped the cement delivery. This residual cement flow may put the patient at risk.

In a particular embodiment, the comparator module 70 evaluates if a minimum volume of cement, for example 0.2 ml, has already been injected and if so, instructs the drive control unit to actuate the motor 18 in reverse for a short period of time before stopping if a stop command is received from the input module 68. The comparator module 70 determines this short period of time such that the movement of the push rod 30 is reversed on a small distance, for example selected from 0.5 mm to 1 mm. In a particular embodiment, the user provides the injection command by maintaining an "inject" button in a depressed position, and provides a stop command when the "inject" button is released; in an alternate embodiment, the user provides the injection command by pressing an "inject" button, and provides a stop command by pressing a "stop" button. In both cases, the input module 68 sends the stop command to the drive control unit 72, and the comparator module 70 instructs the drive control unit 72 to perform a reverse movement before stopping only if the minimum injection volume has been reached. The reverse movement takes place within milliseconds of the end of the delivery phase and eliminates the residual flow such that the cement flow is stopped immediately or substantially immediately after the user's command. If the minimum injection volume has not been reached the drive control unit 72 directly stops the motor 18 upon receipt of the stop command.

It should be understood that the modules illustrated in FIG. 8 may be provided in a single application 66 or a combination of two or more applications coupled to the processor 64. While illustrated in the block diagrams as groups of discrete components communicating with each other via distinct data signal connections, it will be understood by those skilled in the art that the embodiments are provided by a combination of hardware and software components, with some components being implemented by a given function or operation of a hardware or software system, and many of the data paths illustrated being implemented by data communication within an application or operating system.

As mentioned above, once the bone cement is mixed, it undergoes a swelling phase followed by a polymerization phase. Knowing the termination of the swelling phase allows the determination of the point when the toxic monomer has been consumed though the swelling process and the cement forms a cohesive dough which is much easier to handle than a more liquid suspension. When the dough-like cement is delivered in the vertebra the cement usually fills more uniformly with reduced risks of leakage. A monitoring system for determining the end of the swelling phase and the initiation of the polymerization phase has been developed and is described in published PCT application WO 2008/119167 A1, which is incorporated by reference herein.

In the present embodiment, the delivery unit 10 preferably includes such a monitoring system. In a particular embodiment and as illustrated in FIG. 3A, the electro-conductive plates 48, 148 form a capacitor which acts as a cure sensor. The pins 152 provide contact with the processor 64, acting as the electrical source. The control unit 60 thus includes another application 67 running on the processor 64, which determines the capacitive/dielectric changes of a signal passing through the cement from the plates 48: as the cement swells and polymerizes, the capacitive properties of the cement change, and this change is detected by the capacitor because of the changing dielectric properties of the bone cement. The chemical and physical changes of the cement can be displayed on the display unit 14.

Figure 6:
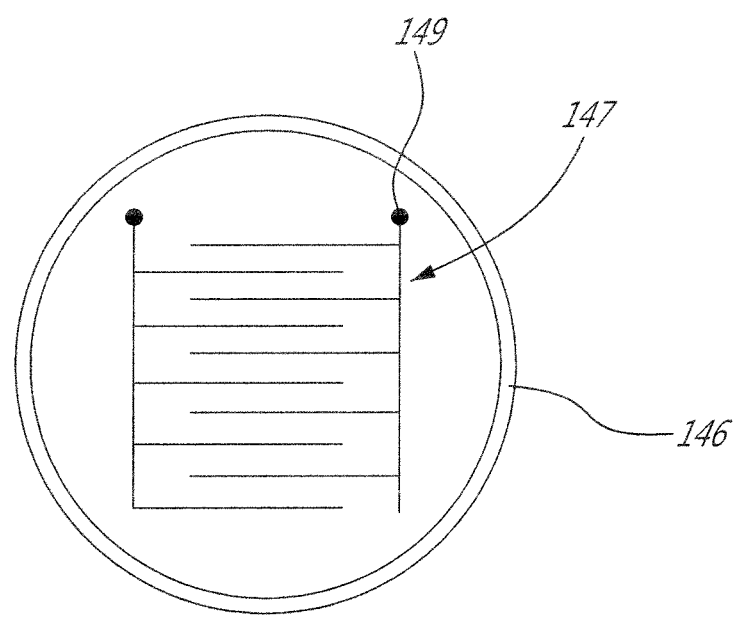
FIG. 6 is an end view of a piston of the reservoir in accordance with an alternate embodiment.

Referring to FIG. 6, in an alternate embodiment, the electro-conductive plates 48, 148 are replaced by interdigitating electrodes 147 which act as the sensor and are located on the tip of the piston 146, on the face in contact with the cement. Each interdigitating electrode 147 resembles a comb with sufficient spacing between individual fingers to accommodate the fingers of the complementary electrode 147. The comb electrodes 147 are preferably plated on the piston 146 using an appropriate electro-less method. Connectors 149 such as pins extend through the piston 146 and out of the opposed face thereof for contact with connectors (not shown) electrically connected to the processor 64. An alternating voltage is applied to the interdigitating electrodes 147 through the connectors 149 and the electrodes 147 produce an electric field extending into the cement. The electrical current is proportional to the attenuation of the electro-conductive cement properties. The polymerization of the cement leads to a reduction of the electrical current due to the increase in the electric resistance of the hardening cement and thus the change in decline in current provides a reading of the cement setting. The application 67 determines the electrical current from the electrodes 147 and its attenuation and from this attenuation determines the chemical and physical changes of the cement, which can be displayed on the display unit 14.

In a particular embodiment, the application 67 determines an inflection point or significant and sudden change in the electrical property being monitored, this inflection point describing the initiation of the polymerization phase. An indication of the initiation of the polymerization phase may be displayed on the display unit 14, as well as the time elapsed since this initiation.

Figure 7:
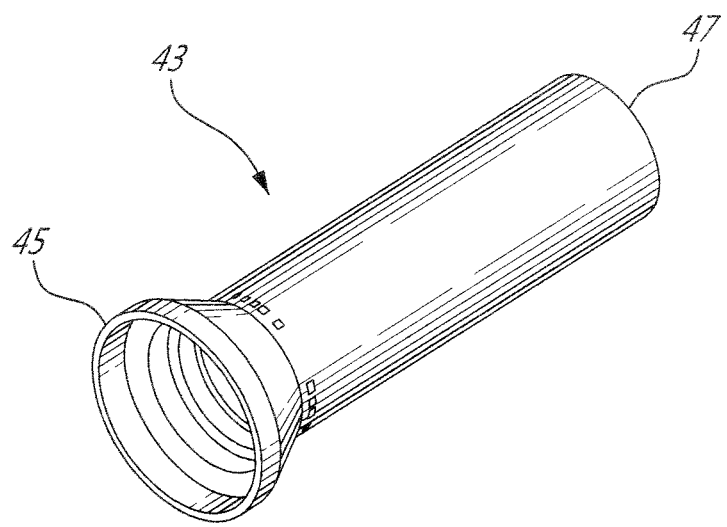
FIG. 7 is an oblique view of a shielding sleeve which may be used with the reservoir of FIGS. 3A-3B.

Referring to FIG. 7, the system also includes a shielding sleeve 43 to cover the reservoir 13 while the curing of the bone cement is being monitored, to reduce interference of the environment on the monitoring process. In a particular embodiment, the shielding sleeve is made of stainless steel, but any other adequate isolating material can alternately be used. The sleeve 43 includes a base 45 defining an open end, and an opposed closed tip 47. The shielding sleeve 43 is sized to contain the reservoir 13, and the base 45 is configured and sized to surround the socket adaptor 34, 134. The base 45 and socket adaptor 34, 134 may optionally include features allowing interlocking of these two components, e.g. complementary threaded portions.

In use, the user mixes the components of the bone cement and fills the reservoir 13. The filled reservoir 13 is then attached to the delivery unit 10, and the first of three successive working modes of the delivery unit 10 may begin. In the first or monitoring mode, the cement swelling and polymerization is monitored. This is performed with the shielding sleeve retained around the reservoir. Once the cement is ready, e.g. as indicated by the monitoring system, the shielding sleeve is removed and the reservoir 13 is attached to the flexible tubing 15, which is connected to the cannula 19 placed in the bone where injection is to be performed.

The second or priming mode begins at the command of the user through the touch pad 16 or equivalent on the remote control unit if provided, and cement is ejected from the reservoir 13 to fill the flexible tube 15 and cannula 19.

Once the priming mode is complete, the third or delivery mode begins at the command of the user through the touch pad 16 or equivalent on the remote control unit if provided. The bone cement is injected into the bone through the cannula 19 until the user indicates, through the touch pad 16 or equivalent on the remote control unit if provided, that the delivery mode is complete, with the push rod 30 reversing slightly before stopping if appropriate, as described above. The cement then completes its hardening phase in the bone. The entire process, from the mixing of the cement components to the complete hardening, can take for example less than 20 minutes, depending on various factors such as the type of cement used, the temperature of the components and the ambient conditions.

During the delivery mode, when the lead screw 22 is rotated by the motor 18 through the pulleys 24, 26, the push rod 30, which is prevented from rotating by its engagement with the guiding track 32, undergoes a linear or sliding displacement. The motor torque is thus transformed into a push force produced on the push rod 30, which is supported by the bearing assembly in the transverse support element 20. The pressurization of the cement in the reservoir 13 due to the force applied by the push rod 30 through the piston 46 causes a significant tensile force in the reservoir walls. These forces are transmitted to the socket adaptor 34, which is stabilized by the support plates 33, 35 connecting the adaptor 34 to the transverse support element 20. The transverse support element 20 is the anchor base through which the motor 18, lead screw 22 and the reservoir 13 (through the support plates 33, 35 and socket adaptor 34) are anchored relatively to each other, and as such is the portion of the delivery unit 10 which takes up the stresses caused by the high injection pressure of the bone cement. The support structure defined by the support plates 33, 35, track 32, transverse support element 20 and socket adaptor 34 is self-sufficient and is designed to handle high forces, for example up to 6000 N, allowing the casing 12 to have a minimal thickness and weight. In a particular embodiment, the delivery unit 10 has a weight of approximately 4 lbs without the reservoir 13.

The embodiments of the invention described above are intended to be exemplary. Those skilled in the art will therefore appreciate that the foregoing description is illustrative only, and that various alternate configurations and modifications can be devised without departing from the spirit of the present invention. Accordingly, the present invention is intended to embrace all such alternate configurations, modifications and variances which fall within the scope of the appended claims.

The invention claimed is:

1. A bone cement delivery unit comprising: a casing having a guide opening defined therethrough;
   a push rod slidable within the casing and out of the casing through the guide opening along an injection direction;
   a motor;
   a transmission system engaged to the motor and the push rod and transmitting power from the motor to the push rod for sliding the push rod along the injection direction; and
   a rigid support structure including:
      a socket adaptor surrounding the guide opening of the casing and configured to engage and retain a bone cement reservoir,
      a support element distinct from the casing and extending within the casing, the support element connected to and supporting the transmission system, and
      at least one support member distinct from the casing and extending within the casing, the at least one support member fixedly interconnecting the socket adaptor and the support element, the at least one support member supporting and guiding the push rod along the injection direction as the push rod slides relative to the at least one support member along the injection direction.

2. The bone cement delivery unit according to claim 1, wherein the motor is fixedly mounted to the support element.

3. The bone cement delivery unit according to claim 1, wherein the support element is a transverse support element extending within the casing transversally with respect to the injection direction.

4. The bone cement delivery unit according to claim 1, wherein the at least one support member includes at least one guide element directing the push rod along the injection direction.

5. The bone cement delivery unit according to claim 1, wherein the at least one support member includes lower and upper support plates distinct from the casing and interconnecting the socket adaptor and the support element with the push rod extending between the lower and upper support plates, the lower and upper support plates extending along the injection direction.

6. The bone cement delivery unit according to claim 1, wherein one of the at least one support member includes a guiding track rigidly connected thereto and extending along the injection direction, the guiding track being engaged to an elongated slot defined in the push rod.

7. The bone cement delivery unit according to claim 1, wherein the transmission system includes a lead screw threadingly engaged to the push rod and rotated by the motor, the lead screw supported by the support element, the push rod being prevented from rotating by the at least one support member such that a rotational movement of the lead screw is transferred into a sliding movement of the push rod.

8. The bone cement delivery unit according to claim 1, including means to receive commands from a user, means to activate the motor to slide the push rod along the injection direction upon receipt of an injection command from the user, means to determine a quantity of bone cement pushed out of the reservoir, and means to activate the motor to slide the push rod in a direction opposite of the injection direction along a predetermined distance before stopping the movement of the push rod upon receipt of a stop command from the user if the quantity of the bone cement pushed out of the reservoir has reached at least a predetermined minimum value.

9. The bone cement delivery unit according to claim 1, including a control unit comprising:
   an input module adapted to receive user commands from a user-activated input device;
   a comparator module adapted to send a reverse command if a quantity of cement pushed out of the reservoir exceeds a predetermined minimum value; and
   a drive control unit adapted to activate the motor to slide the push rod in the injection direction upon receipt of an injection command from the input module, to directly stop the motor upon receipt of a stop command from the input module when the reverse command is not received, and to stop the motor after activating the motor to slide the push rod in a direction opposite of the injection direction along a predetermined distance upon receipt of the stop command from the input module and of the reverse command from the comparator module.

10. A bone cement delivery unit according to claim 1, further comprising a control unit and the cement reservoir having a proximal end configured to engage the socket adaptor, the socket adaptor including members electrically connected to the control unit, the cement reservoir including a sensor for monitoring curing of the bone cement, the members of the adaptor being in electrical contact with the sensor when the proximal end is engaged to the adaptor.

11. The bone cement delivery unit according to claim 10, wherein the sensor includes two opposed electro-conductive plates both attached to an outer surface of the cement reservoir or both attached to an inner surface of the cement reservoir.

12. The bone cement delivery unit according to claim 10, wherein the cement reservoir includes a piston slidable therein and connected to the push rod, and the sensor includes two interdigitating electrodes attached to a face of the piston in contact with the bone cement.

13. The bone cement delivery unit according to claim 10, wherein the members include spring-loaded pins extending from the adaptor to form an electrical contact with the sensor.

14. The bone cement delivery unit according to claim 1, wherein the support element is connected to the casing.

15. The bone element delivery unit according to claim 1, wherein the socket adaptor is distinct from the casing.

* * * * *